(12) United States Patent
Konduri et al.

(10) Patent No.: US 8,501,962 B2
(45) Date of Patent: Aug. 6, 2013

(54) PROCESS FOR THE PREPARATION OF HIGH PURITY SUNITINIB AND ITS PHARMACEUTICALLY ACCEPTABLE SALT

(75) Inventors: Srinivasa Krishna Murthy Konduri, Hyderabad (IN); Bhujanga Rao Adibhatla Kali Satya, Hyderabad (IN); Nannapaneni Venkaiah Chowdary, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 69 days.

(21) Appl. No.: 13/000,126

(22) PCT Filed: Nov. 17, 2008

(86) PCT No.: PCT/IN2008/000772
§ 371 (c)(1),
(2), (4) Date: Dec. 20, 2010

(87) PCT Pub. No.: WO2009/157011
PCT Pub. Date: Dec. 30, 2009

(65) Prior Publication Data
US 2011/0092717 A1    Apr. 21, 2011

(30) Foreign Application Priority Data
Jun. 23, 2008 (IN) .......................... 1529/CHE/2008

(51) Int. Cl.
*C07D 209/34* (2006.01)
(52) U.S. Cl.
USPC ........................................................ 548/468
(58) Field of Classification Search
USPC .................................................. 548/468
See application file for complete search history.

(56) References Cited

U.S. PATENT DOCUMENTS

| 6,878,733 B1 | 4/2005 | Shenoy et al. |
| 2004/0266843 A1 | 12/2004 | Howlett et al. |
| 2006/0009510 A1 | 1/2006 | Havens et al. |

FOREIGN PATENT DOCUMENTS

| WO | WO 01/60814 A2 | 8/2001 |
| WO | WO 03/035009 A2 | 5/2003 |
| WO | WO 03/070725 A2 | 8/2003 |

OTHER PUBLICATIONS

Fischer, H., "2,4-Dimethyl-3,5-Dicarbethoxypyrrole [2,4-Pyrroledicarboxylic acid, 3,5- dimethyl-, diethyl ester]," Organic Synthesis, Coll. vol. 2, p. 202 (1943).
Genin, M. et al., "Design, Synthesis, and X-ray Crystallographic Analysis of Two Novel Spirolactam Systems as β-Turn Mimics," J. Org. Chem., 58:860-66 (1993).
Manley, J. et al., "Early Amidation Approach to 3-[(4-Amido)pyrrol-2-yl]-2-indolinones," J. Org. Chem., 68:6447-50 (2003).
McIntyre, J., "Sunitinib Malate; Oncolytic Drug; Multitargeted Tyrosine Kinase Inhibitor," Drugs of the Future, 30(8):785-92 (2005).
Vaidyanathan, R. et al., "Amidations Using N,N'-Carbonyldiimidazole: Remarkable Rate Enhancement by Carbon Dioxide," J. Org. Chem., 69:2565-68 (2004).
Carpino, L., "1-Hydroxy-7-azabenzotriazole. An Efficient Peptide Coupling Additive," J. Am. Chem. Soc. 115:4397-4398 (1993).
Miyazawa, T. et al., "Effect of copper(II) chloride on suppression of racemization in peptide synthesis by the carbodiimide method," Int. J. Peptide Protein Res. 39:234-244 (1992).

*Primary Examiner* — Shawquia Young
(74) *Attorney, Agent, or Firm* — Kilpatrick Townsend & Stockton LLP

(57) ABSTRACT

The present invention relates to an improved process for the preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib base of formula (I) and its pharmaceutically acceptable malate salt of formula (I(a)).

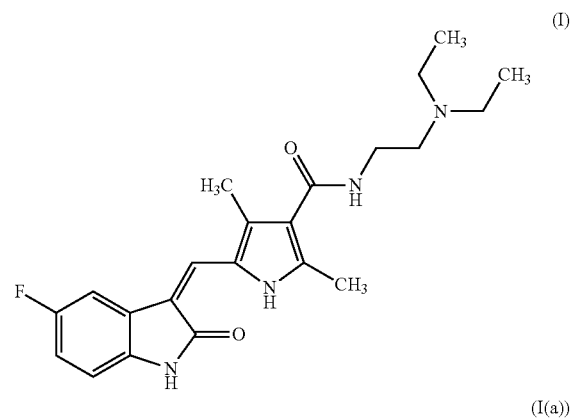

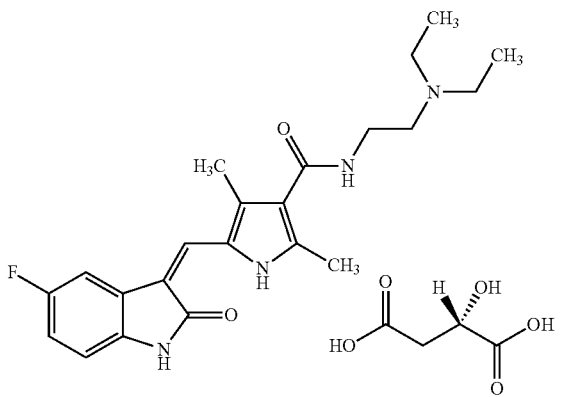

36 Claims, No Drawings

PROCESS FOR THE PREPARATION OF HIGH PURITY SUNITINIB AND ITS PHARMACEUTICALLY ACCEPTABLE SALT

The present invention relates to an improved process for the preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib base of formula-I and its pharmaceutically acceptable malate salt of formula-I(a).

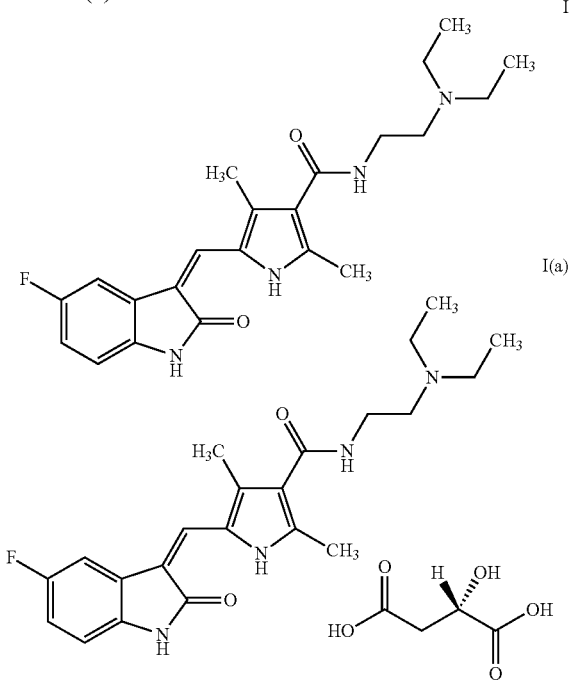

Sunitinib malate of formula-I(a) is a small molecule inhibitor of multiple receptor kinases involved in cancer, including vascular endothelial growth factor receptors, platelet derived growth factor receptors and the KIT receptor. It has been recently approved by the US FDA for the treatment of Gastro Intestinal Stromal Tumors (GIST) and Advanced Renal Cell Carcinoma (RCC).

Studies revealed that Sunitinib malate (SUTENT®) is an oral, multi-targeted tyrosine kinase inhibitor (TK1) that targets and blocks the signaling pathways of multiple selected receptor tyrosine kinases (RTKs).

Sunitinib exists as yellow to orange powder. Sunitinib is a non-hygroscopic substance and has no chiral center, however the final substance is optically active due to malate part of the molecule.

BACKGROUND OF THE INVENTION

Sunitinib base is having the chemical name N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide is also known as SU11248 and similar pyrrole derivatives are first disclosed in WO01/060814. Its equivalent patent is U.S. Pat. No. 6,573,293.

The aforesaid patent describes a process for the preparation of Sunitinib as shown in Scheme-1 below.

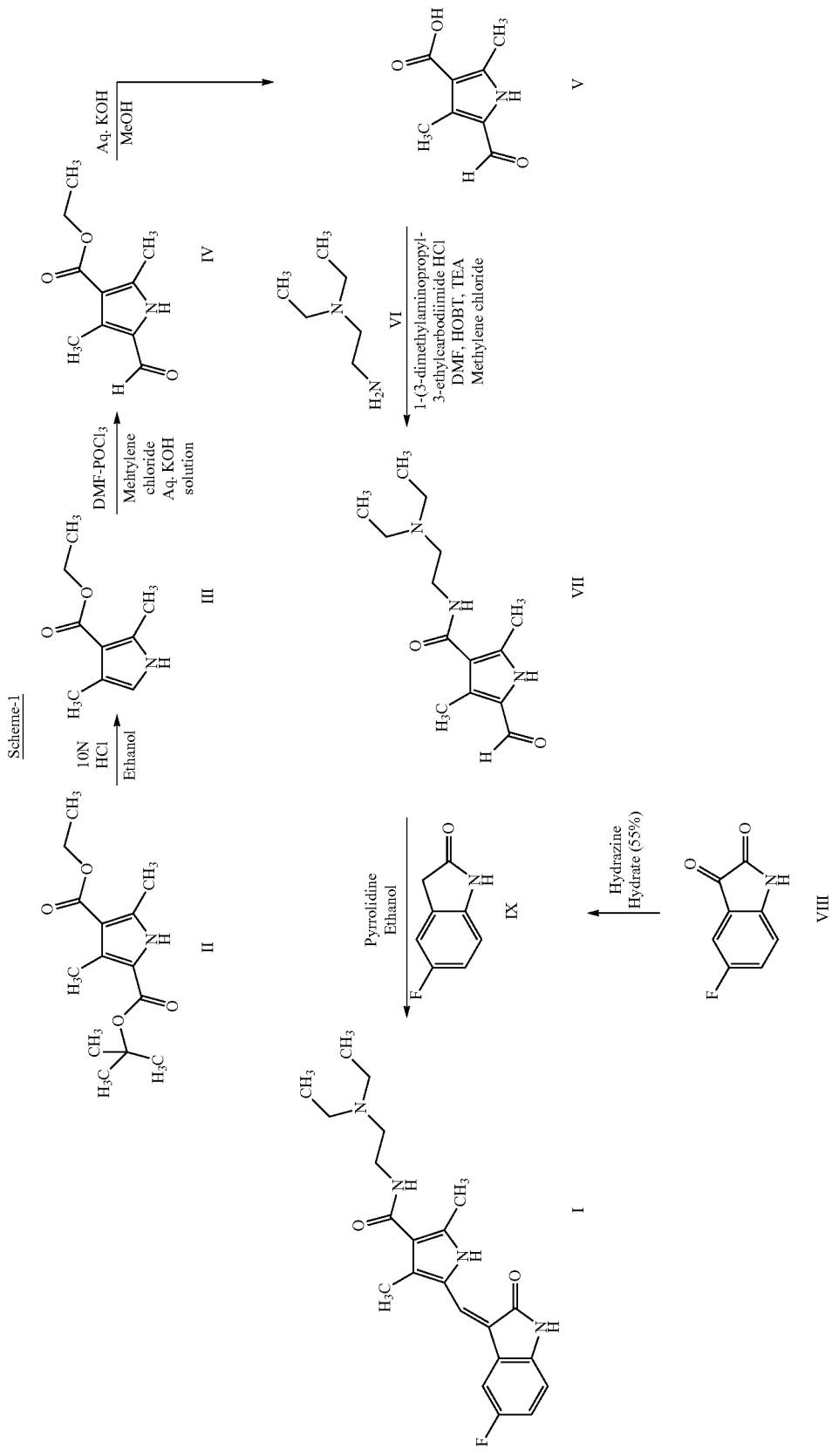

Accordingly,

In the U.S. Pat. No. 6,573,293, the intermediate of formula II (R=t-Bu) is prepared as procedure described in Org. Synthesis. Coll. Vol. 2, p. 202 (Scheme-I(a)) for similar compound (R=Et).

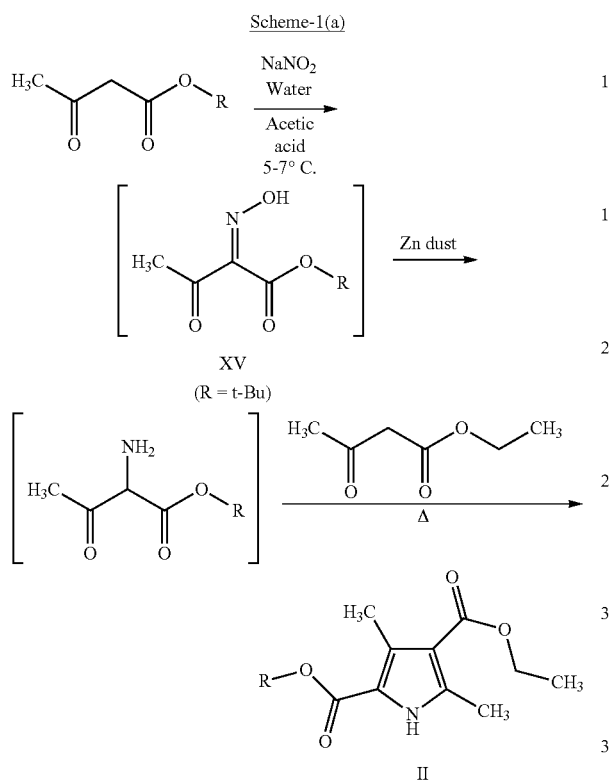

R = Et (*Org. Synth. Coll.* Vol., 2, p 202)
R = t-Bu (US 6573293, only structure indicated, no process disclosed)

Later it is selectively decarboxylated in the presence of aqueous alcoholic HCl to get half-ester pyrrole derivative of formula-III.

The compound of formula-III is then formylated by a known synthetic methodology using DMF-POCl$_3$ complex to get the formylated ester derivative of formula-IV.

The ester functionality of derivative of formula-IV is selectively hydrolyzed to get a carboxylic acid derivative of formula-V.

The carboxylic acid derivative of formula-V is then selectively converted to amide of formula-VII using 2-(Diethylamino ethylamine of formula-VI in the presence of 1-(3-dimethylaminopropyl-3-ethylcarbodiimide HCl.

The 5-fluoro-2-oxindole derivative of formula-IX is prepared by the selective reduction of carbonyl functionality of the compound of formula-VIII using 55% hydrazine hydrate. Finally the formyl derivative of formula-VII is coupled with 5-Fluoro-2-oxindole of formula-IX by Knoevenagel method using pyrrolidine as a catalyst to get Sunitinib base of formula-I. The product is characterized by $^1$H NMR and Mass spectral analysis.

Later the same inventors in the year 2003 disclosed a procedure (Scheme-2) similar to the earlier patent (WO01/060814) with some slight modification. In this patent (WO2003035009), the formylated derivative of formula-V is first reacted with 5-Fluoro-2-oxindole of formula-IX under Knoevenagel conditions using piperidine as a catalyst to get the carboxylic acid derivative of formula-X.

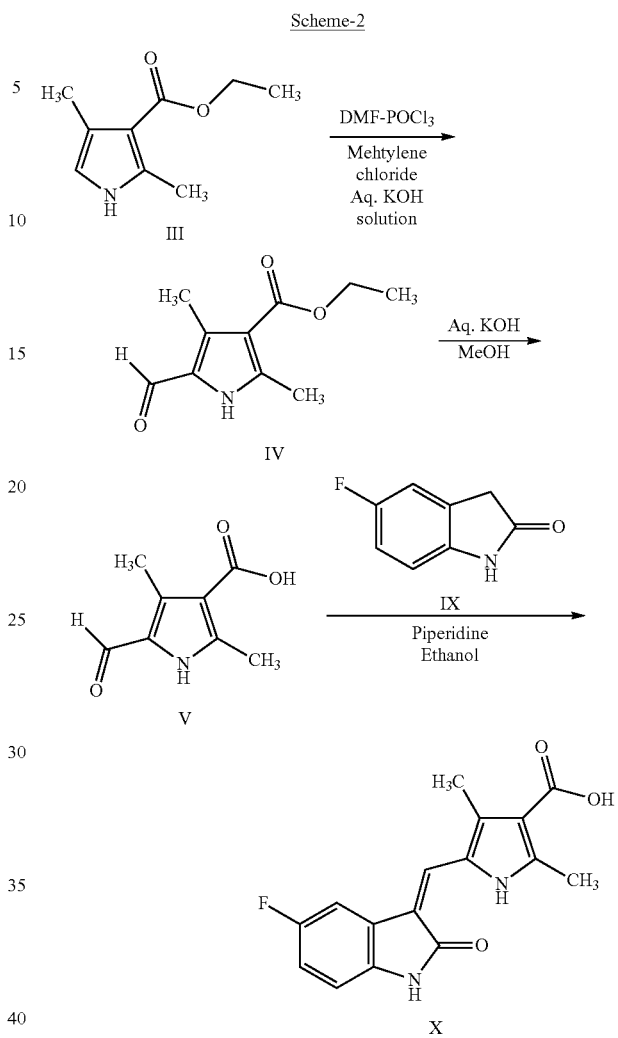

In the same year (2003), a different synthetic methodology (Scheme 3) is disclosed in WO2003070725. In this patent, an imidazole-amide derivative of formula-XI is prepared using carboxylic acid derivative of formula-V in presence of CDI. The resulting imidazole-amide derivative of formula-XI is reacted with N,N-Diethylaminoethylamine of formula-VI to get imine-amide derivative of formula-XII and its in-situ condensation with 5-Fluoro-2-oxindole of formula-IX in acetonitrile at 60° C. for 18 hours affords Sunitinib base of formula-I. Later the method of synthesis is published in J. Org. Chem., 2004, 69, 2565-2568.

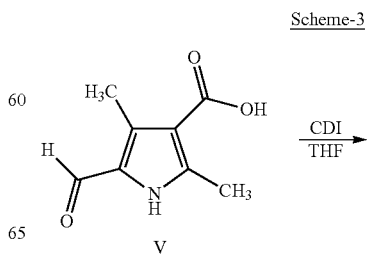

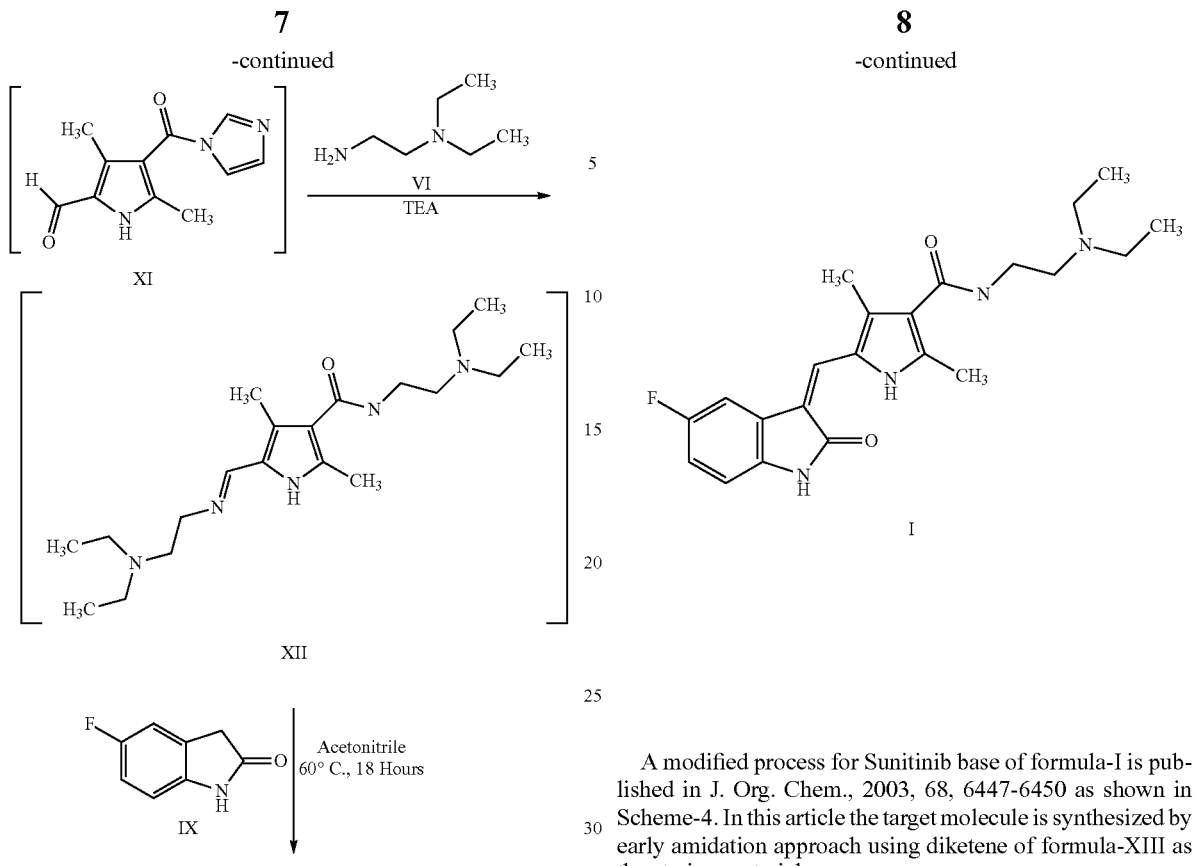
A modified process for Sunitinib base of formula-I is published in J. Org. Chem., 2003, 68, 6447-6450 as shown in Scheme-4. In this article the target molecule is synthesized by early amidation approach using diketene of formula-XIII as the staring material.

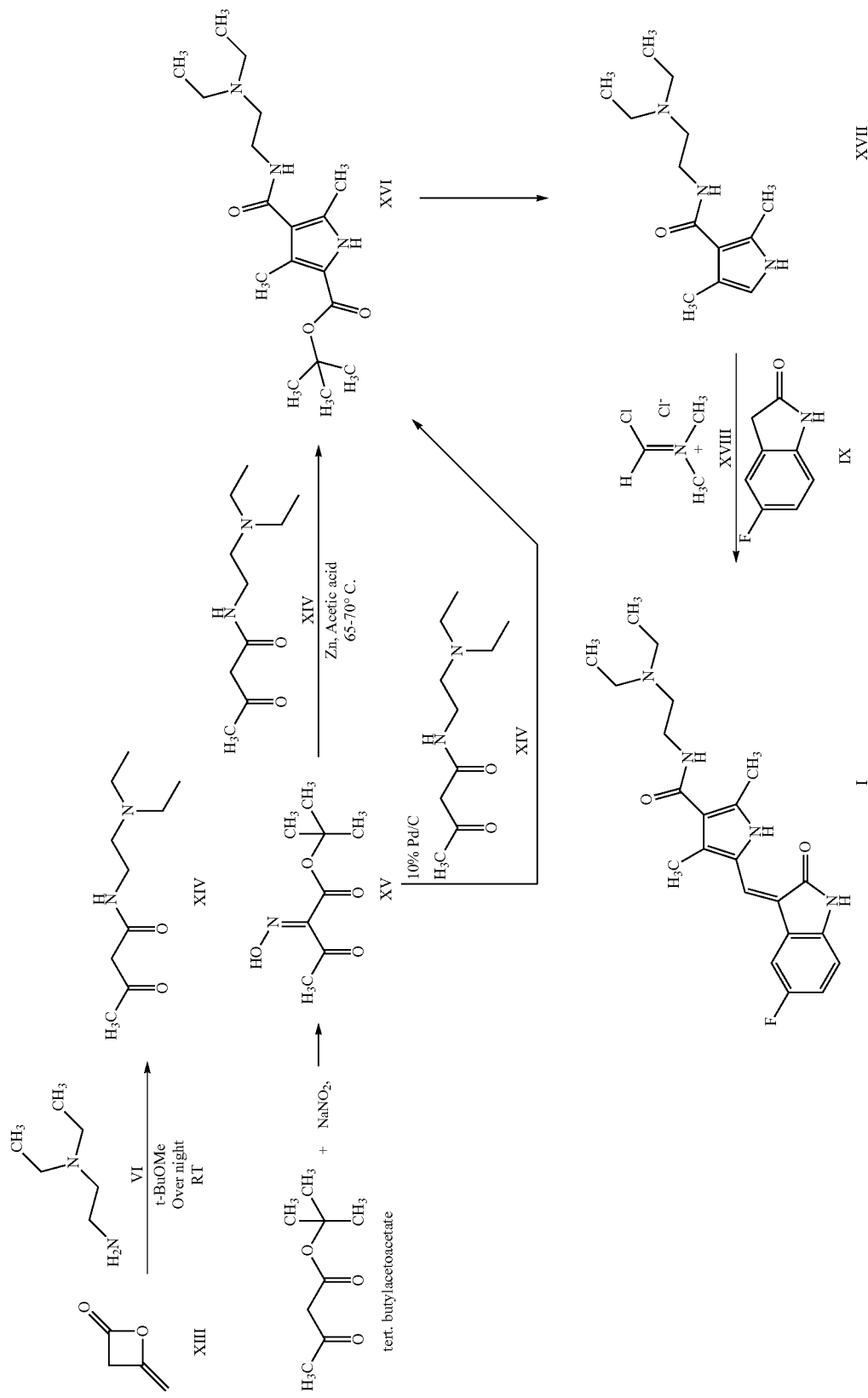

Process disclosed in the first patent (U.S. Pat. No. 6,573,293 and WO01/060814) for the preparation of Sunitinib base of formula-I has the following disadvantages.
(a) The chemical purity of the intermediates and final product is not disclosed.
(b) In this patent, the intermediate of formula II (R=t-Bu) is prepared as described in Scheme-I(a).
According to the method of synthesis, tert. butyl acetoacetate and sodium nitrite are reacted at 5-7° C. in acetic acid. The resulting oxime derivative of formula-XV (R=t-Bu) is then condensed and cyclized with ethyl acetoacetate using Zn dust as reducing agent and refluxed at 115-120° C. The product is crystallized in 95% alcohol to get the intermediate of formula-II. Using the above method of synthesis for formula-II, the following disadvantages are encountered.
(i) Yields are not reproducible. By following the same experimental conditions, only 30% yield against 57-64% reported yield is obtained. The low yields may be due to elevated temperatures (115-120° C.) during condensation and cyclization.
(ii) A number of impurities are formed during condensation and cyclization at higher temperatures.
(iii) Considerable frothing is observed while heating the reaction to 115-120° C. which is uncontrollable.
(iv) On bigger scale, decantation is not a suitable operation at higher temperatures.
(v) Work-up procedure is not suitable for plant scale operation.
(vi) We observed that, separation of impurities from the intermediate of formula-II is not easy. It requires number of crystallizations to remove the impurities. This would lead to poor recovery of the wanted intermediate of formula-II.
(c) Yields are not reproducible in making of formula-III. Since we observed that elevated temperatures (67° C.) reduce yield and purity of the intermediate of formula-III.
(d) In making intermediate of formula-IV, V & VII, very toxic and hazardous solvent methylene chloride would increase pollution load.
(e) Filtration of intermediate of formula-IV as stipulated in the patent WO01/060814, below 15° C. is very difficult since the intermediate forms a pasty mass at this temperature.
(f) Expensive reagent like 1-(3-dimethylamino-aminopropyl-3-ethyl carbodimide hydrochloride is used in the synthesis of compound of formula-VII, which is not commercially available reagent and recyclable. Also it poses lot of pollution.
(i) Very low yields are reported.
(ii) Highly flammable solvents (hexane and diethyl ether) are used in isolation.
(iii) Multiple solvents are used in the synthesis of formula-VII.
(g) In the synthesis of 5-fluoro-2-oxindole of formula-IX, 55% hydrazine hydrate is used to reduce the carbonyl functionality at $3^{rd}$ position of 5-fluoro isatin of formula-VIII.
(i) Yields are not reproducible.
(ii) Lot of frothing is observed during reaction at 110° C. This is due to low concentration (55%) of hydrazine hydrate.
(h) In the penultimate step, i.e., condensation of 5-fluoro-2-oxindole of formula-IX with aldehyde derivative of formula-VII, no elaborate solvent study is performed.
(i) Purity of the Sunitinib base of formula-I is not disclosed.
(i) No experimental details for the synthesis of Sunitinib malate of formula-I(a) is disclosed.

Process disclosed in the second patent (WO2003035009) for the preparation of Sunitinib base has the following disadvantages.
(a) In making intermediates of formula-IV & V, very toxic and hazardous solvent methylene chloride would increase the pollution loads.
(b) Filtration of intermediate of formula-IV below 15° C. is very difficult, since the nature of the intermediate is pasty.
(c) In making of formula-X, yields are not reproducible during condensation of compound of formula-V with 5-fluoro-2-oxindole of formula-IX in piperidine/ethanol medium.
(d) Several impurities are encountered during synthesis of formula-X.
(e) No experimental details are given for Sunitinib base of formula-I starting from formula-X.
(f) No experimental details for Sunitinib malate of formula-I(a) is disclosed.

Process disclosed in the third patent (WO2003070725) for the preparation of Sunitinib base has the following disadvantages.
(a) Usage of carbonyl diimidazole in the synthesis of formula-XI would leads to cost escalation of the final product.
(b) No experimental details for the synthesis of Sunitinib malate of formula-I(a) is disclosed Process disclosed in the fourth patent (US2006009510) for the preparation of Sunitinib base of formula-I has the following disadvantages.
(a) Highly toxic reagent like diketene is used in the synthesis, which is not commercially available and handling of such a chemical on industrial scale unviable.
(b) Expensive catalyst like 10% Pd/C is used in the synthesis.
(c) Unstable reagent like chloromethylenedimethylammonium chloride is used for formylation.
(d) No experimental details for the synthesis of Sunitinib malate of formula-I(a) is disclosed.

BRIEF DESCRIPTION OF THE PRESENT INVENTION

Sunitinib malate is an FDA approved anti-cancer agent that has now been on the market and has shown great promise with few side effects. Keeping in view of the difficulties in commercialization of the known processes for the preparation of Sunitinib malate, we aimed to develop a simple, economical, environmental friendly process for commercial production of Sunitinib malate.

Due to poor solubility of Sunitinib base of formula-I in ethanol or methanol, very large volume of solvent is required to crystallize Sunitinib base. Hence a better process for preparation of high purity of Sunitinib base directly obtainable from the reaction mixture is highly desirable. In that direction a detailed study was taken-up.

We observed that a promising approach for such a process is to:
(i) avoid high temperature conditions (115-120° C.) in preparation of compound of formula-II
(ii) minimization of frothing by carrying out the reaction at moderate temperatures (70-75° C.)

(iii) avoid decantation at higher temperatures in the preparation of compound of formula-II
(iv) usage of suitable solvent for extraction during work-up of compound of formula-II to increase the yield
(v) usage of suitable solvent for isolation of intermediate of formula-II
(vi) avoid higher temperatures in the preparation of compound of formula-III
(vii) usage of effective solvent system to achieve high yields consistently
(viii) avoid toxic and hazardous solvent like methylene chloride from the process
(ix) eliminate usage of highly flammable solvents like hexane and diethyl ether from the process
(x) avoid filtration at low temperatures in the preparation of formula-IV to overcome the filtration problem
(xi) eliminate the usage of expensive reagent like 1-(3-dimethylamino-aminopropyl)-3-ethyl carbodimide hydrochloride in the preparation of formula-VII
(xii) usage of commercially available, easily recoverable and recyclable coupling agent like dicyclohexyl carbodimide in making of formula-VII
(xiii) avoid the usage of multiple solvents in the preparation of formula-VII
(xiv) usage of 90% aqueous hydrazine hydrate in place of 55% hydrazine hydrate to overcome frothing problem
(xv) avoid the usage of highly toxic reagent like diketene in the process
(xvi) avoid the usage of expensive catalyst like 10% Pd/C in the process
(xvii) avoid the usage of highly unstable and moisture sensitive reagent like chloromethylenedimethylammonium chloride in the process Accordingly the main objective of the present invention is to provide an improved process for the preparation of Sunitinib malate of formula-I(a) by avoiding high temperature conditions (115-120° C.) in the preparation of the intermediate of formula-II. Accordingly another objective of the present invention is to provide an improved process for the preparation of Sunitinib malate of formula-I(a) by minimizing of frothing by doing the reaction at moderate temperatures of the order of 70-75° C. in the preparation of formula-II.

Accordingly yet another objective of the present invention is to provide an improved process for the preparation of Sunitinib malate of formula-I(a) by avoiding decantation at higher temperatures in the preparation of compound of formula-II Accordingly still another objective of the present invention is to provide an improved process for the preparation of Sunitinib malate of formula-I(a) by employing suitable solvent for extraction during work-up stage of the intermediate of formula-II to increase the yield.

Accordingly another objective of the present invention is to provide an improved process for the preparation of Sunitinib malate of formula-I(a) by employing suitable solvent system for isolation of the intermediate of formula-II.

Accordingly another objective of the present invention is to provide an improved process for the preparation of Sunitinib malate of formula-I(a) by avoiding higher temperatures in the preparation of compound of formula-III.

Accordingly another objective of the present invention is to provide an improved process for the preparation of Sunitinib malate of formula-I(a) by employing effective solvent system like isopropyl alcohol to improve the yield during the preparation of compound of formula-III.

Accordingly another objective of the present invention is to provide an improved process for the preparation of Sunitinib malate of formula-I(a) by avoiding toxic and hazardous solvent like methylene chloride from the entire process.

Accordingly yet another objective of the present invention is to provide an improved process for the preparation of Sunitinib malate of formula-I(a) by avoiding the usage of highly flammable solvents like hexane and diethyl ether in the process.

Accordingly another objective of the present invention is to provide an improved process for the preparation of Sunitinib malate of formula-I(a) by avoiding filtration at low temperatures in the preparation of intermediate of formula-IV to overcome the filtration problem.

Accordingly yet another objective of the present invention is to provide an improved process for the preparation of Sunitinib malate of formula-I(a) by avoiding the usage of expensive reagent like 1-(3-dimethylamino-aminopropyl)-3-ethyl carbodimide hydrochloride in the preparation of intermediate of formula-VII.

Accordingly another objective of the present invention is to provide an improved process for the preparation of Sunitinib malate of formula-I(a) by using of commercially available, easily recoverable and recyclable coupling agent like dicyclohexyl carbodimide in making compound of formula-VII.

Accordingly yet another objective of the present invention is to provide an improved process for the preparation of Sunitinib malate of formula-I(a) by avoiding the usage of multiple solvents in the preparation of the intermediate of formula-VII.

Accordingly still another objective of the present invention is to provide an improved process for the preparation of Sunitinib malate of formula-I(a) by avoiding the usage of 55% hydrazine hydrate to overcome frothing problem.

According to still another objective of the present invention is to provide an improved process for the preparation of Sunitinib malate of formula-I(a) by avoiding the usage of highly toxic reagent like diketene in the process.

According to yet another objective of the present invention is to provide an improved process for the preparation of Sunitinib malate of formula-I(a) by avoiding the usage of expensive catalyst like 10% Pd/C in the process.

Yet another objective of the present invention is to provide an improved process for the preparation of Sunitinib malate of formula-I(a) by avoiding the usage of highly unstable and moisture sensitive reagent like chloromethylenedimethylammonium chloride in the process. According to another objective of the present invention is to provide an improved process for the preparation of Sunitinib malate of formula-I(a) by minimizing pollution to a greater extent by employing commercially available environmental friendly reagents and solvents.

According to yet another objective of the present invention is to provide an improved process for the preparation of Sunitinib malate of formula-I(a) by minimizing impurities and solvent residues in the preparation of Sunitinib malate of formula-I(a)

Still another objective of the present invention is to provide an improved process for the preparation of Sunitinib malate of formula-I(a), which produces Sunitinib malate of purity exceeding 99.7%.

Still another objective of the present invention is to provide an improved process for the preparation of Sunitinib malate of formula-I(a), which maintains levels of unknown impurities below 0.10%.

DETAILED DESCRIPTION OF THE PRESENT INVENTION

Schematic representation of present process invention is as given Scheme-5 below. Accordingly,

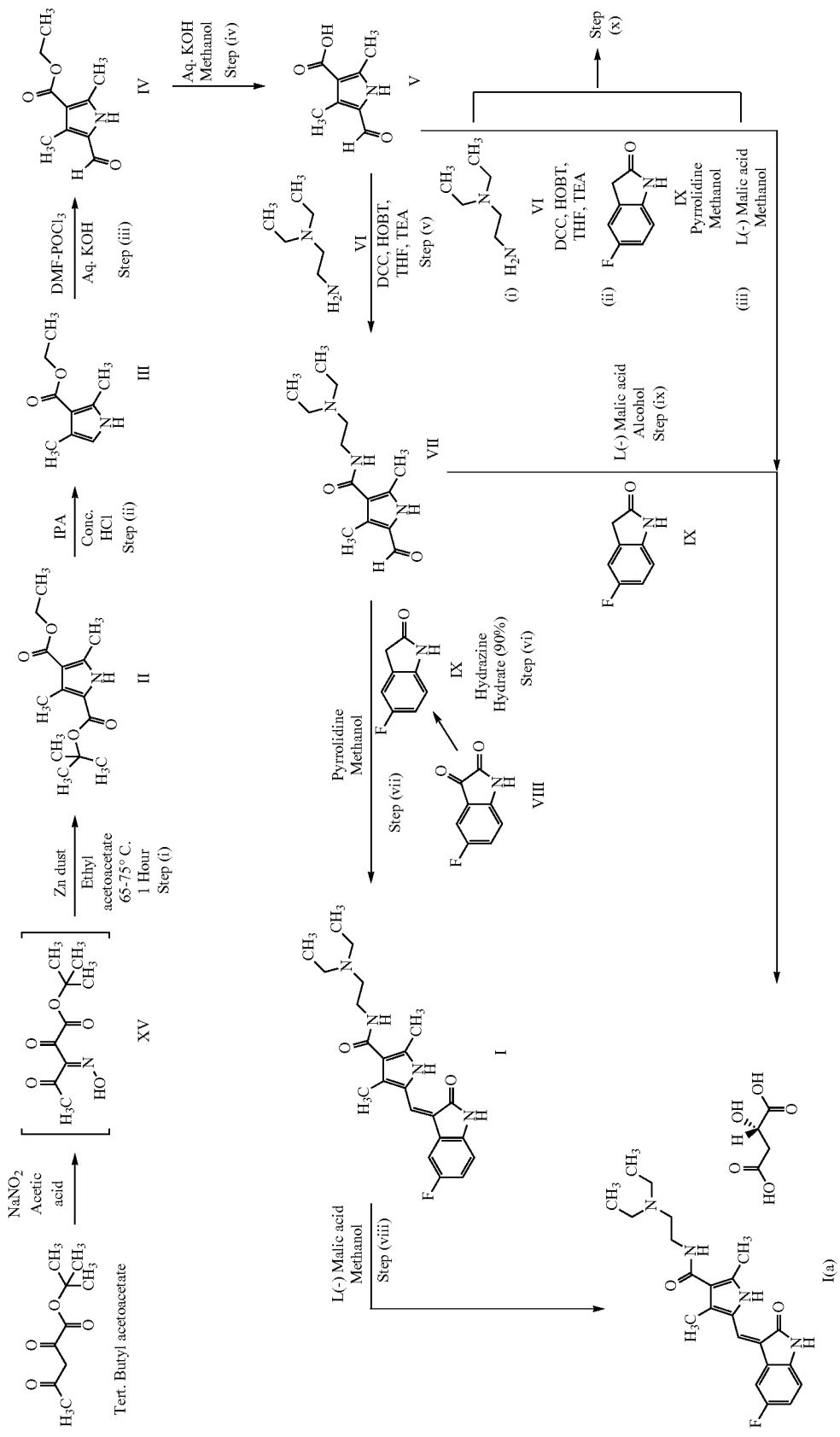

tertiary butyl acetoacetate is reacted with sodium nitrite in the presence of acetic acid medium at 0-5° C. for 5 hours and the resulting oxime derivative of tertiary butyl acetoacetate of formula-XV is in-situ reduced with Zn dust and condensed with ethylacetatoacetate. The product solution is then poured into a beaker containing ice-water. The compound of formula-II can be extracted with ethyl acetate, clarified with charcoal and followed by distillation of the ethyl acetate to get diester derivative of formula-II. The compound of formula-II can be isolated using 95% alcohol. The alcohol may be methanol, ethanol or isopropyl alcohol. The crystalline derivative of formula-II is having HPLC purity >99.5%. The yield obtained is ranging from 60-65%. According to prior art method of synthesis (Org. Synth., II, p 202) for similar compound of formula-II in Scheme-I(a) (R=Et), the compound of formula-II is prepared at higher temperatures. Using the method of synthesis, considerable frothing is observed at higher temperatures. Moreover at higher temperatures, several impurities are formed and are very difficult to purify the material. Also the yield is only 35% as against 64% yield. Therefore, with respect to yield and purity of the product, the present process is more suitable for large-scale operation.

Selective decarboxylation of compound of formula-II in polar solvents like methanol, ethanol or isopropyl alcohol-aq. HCl medium preferably isopropyl alcohol-aq. HCl medium at a temperature ranging between 35-50° C. preferably 45-50° C. gave the crystalline mono ester derivative of formula-III as a purple coloured solid. The compound of formula-III is having HPLC purity of >95%. The yield obtained is ranging from 75-80%. According to prior art (WO 2001/060814) method of synthesis, the compound of formula-III is prepared in ethanol-aq. HCl medium and the temperature of the reaction is 67° C. The obtained product of formula-III is having a purity of <80% only. The yield obtained is only 70-75% as against reported yield 87%. The low yield and low purity may be due to formation of 2,4-dimethylpyrrole during the synthesis. Therefore, with respect to yield and purity of the product, the present process is more suitable for large-scale operation.

The crystalline mono ester derivative of formula-III is then converted to formyl-ester derivative of formula-IV using DMF-POCl$_3$ complex. The resulting formyl derivative is then quenched with ice water. The aqueous solution is then pH adjusted to get bright yellow crystalline solid of formula-IV. According to prior art (WO01/060814) method of synthesis, highly toxic and hazardous solvent (methylene chloride) is used in the reaction. And also there is a mention about sharp rise in temperature from 15° C. to 40° C. during separation of layers. By following the reported method of synthesis, only 84% yield is obtained as against reported yield 100%. Keeping in view of the large-scale operation, the highly toxic and hazardous solvent like methylene chloride usage is omitted. The main advantage of the above described method of synthesis of formula-IV, the yield percentage is >92% and is environmental friendly since solvent extraction is completely omitted. The HPLC purity of the product is 99.9%.

The crystalline yellow solid product of formula-IV is then subjected to base hydrolysis using aqueous alcoholic KOH, followed by solvent extraction using ethyl acetate and subsequent generation of the derivative of formula-V by adjusting the pH to 4.0. The resulting solution is then stirred at 25-30° C. and filtered to get yellow crystalline intermediate of formula-V. According to prior art (WO01/060814) method of synthesis, highly toxic and hazardous solvent like methylene chloride is used for extraction purpose. And the filtration is carried out below 15° C. which is very tedious because of the slimy nature of the product. The yield obtained in our hands is only 60% as against reported 93.5%. To overcome the difficulties associated with the prior art method of synthesis like extraction with highly toxic and hazardous solvent methylene chloride and filtration of the product below 15° C., environmental friendly solvent like ethyl acetate is used for extraction purpose. To avoid filtration problem, the product solution is filtered at room temperature (25-30° C.). At this temperature, filtration is much faster since the nature of the material is crystalline. The main advantages of the above described method of synthesis of formula-V are, the yield percentage is >90% and the filtration is much faster. The HPLC purity of the product is 99.9%.

The yellow crystalline derivative of formula-V is then converted to amide of formula-VII using 2-diethylaminoethyl amine of formula-VI. The coupling agent used in the synthesis is dicyclohexyl carbodimide and, solvent used is tetrahydrofuran. According to prior art (WO01/060814) process, the coupling agent used in the synthesis is 1-(3-dimethylamino-aminopropyl)-3-ethyl carbodimide hydrochloride, which is expensive, commercially not available and a non-recyclable agent. The solvent used in the reported synthesis is dimethyl formamide (DMF). The derivative of formula-VII, being the key penultimate stage intermediate, DMF is not the preferred solvent as it is extremely difficult to remove the last traces. Moreover apart from DMF, highly flammable multiple solvents like n-hexane and diethyl ether are used during isolation process. The yield obtained by following present process is >50% as against 43% reported. Its HPLC purity is 99.95%.

Another penultimate stage intermediate of formula-IX is prepared by reducing the carbonyl functionality of 5-fluoro isatin of formula-VIII using aqueous hydrazine hydrate. According prior art (WO01/060814) process, 55% hydrazine hydrate is used to reduce 5-fluoro isatin. During our study, 55% hydrazine hydrate is found to be not suitable for the synthesis of formula-IX. During heating lot of frothing is observed because of nitrogen gas evolution. It is very difficult to control particularly in large-scale operation. Hence the percentage of hydrazine hydrate is increased to 90%. With this percentage of hydrazine hydrate, the solids easily go into solution during heating, frothing is considerably minimized, and the process can be applied to large-scale operation. The yield obtained by this method of synthesis is more than 75% and the HPLC purity of the product is 99.87%.

The derivative of formula-VII is condensed with 5-fluoro-2-oxindole of formula-IX in methanol medium using pyrrolidine as a catalyst to get Sunitinib base of formula-I. In the prior art (WO01/060814) process, the intermediates were condensed in the presence of ethanol medium using pyrrolidine as a catalyst. By following the reported method of synthesis only 70% yield is obtained as against 88% reported yield where as the present method of synthesis produces more than 78% yield. The HPLC purity of the compound of formula-I is >99.75% and related impurities are well within acceptable limits (0.10%).

During our experimental work on the reactivity of Sunitinib base in various solvents, surprisingly a wide variety of solvents are found to be useful for condensation reaction. Also, surprisingly the condensation of aldehyde-amide derivative of formula-IX with 5-Fluoro-2-oxindole of formula-IX is found to proceed even in the absence of a catalyst. However, certain basic and acidic catalysts are found to hasten the reaction and improve the yields. These catalysts include inorganic bases like ammonia, alkali metal or alkaline earth hydroxides, carbonates, phosphates, bicarbonates and alkali metal hydroxides viz sodium hydroxide, potassium hydroxide or alkaline earth metal hydroxides viz calcium hydroxide, magnesium hydroxide or barium hydroxide, methanolic or ethanolic ammonia, quaternary ammonium compounds like tetra butyl ammonium hydroxide, benzyltrimethyl ammonium hydroxide, silica gel, sodium acetate, ammonium acetate or Lewis acids like Boron trifluoride etherate and organic bases like piperidine, piperazine, sodium ethoxide, sodium methoxide and para toluene sulfonic acid (PTSA).

The final step of the process is conversion of Sunitinib base into its pharmaceutically acceptable malate salt of formula-I (a) using L(-)-malic acid in methanol medium. The method of synthesis of the pharmaceutically acceptable malate salt is not disclosed in the patent WO01/060814. The present method of synthesis of Sunitinib malate is industrially viable process. Its HPLC purity is more than 99.7%. The percentage of related impurities are well within acceptable limits (0.10%). The yield percentage of Sunitinib malate of formula-I(a) is more than 91%.

Alternatively, Sunitinib malate of formula-I(a) can be prepared in one-pot using compound of formula-VII, 5-fluoro-2-oxindole of formula-IX, L(-)-malic acid in methanol medium. The yield obtained using this alternate route of synthesis is >70%. The purity of the product of formula-I(a) is more than 99.5%

Alternatively, Sunitinib malate of formula-I(a) can also be synthesized in one-pot using compound of formula-V, 2-diethyl aminoethylamine of formula-VI, 5-fluoro-2-oxindole of formula-IX, L(-)-malic acid in methanol or tetrahydrofuran medium. The yield obtained using this method of synthesis is more than 60%. The purity of the product of formula-I (a) is more than 99.2%

Accordingly, the present invention provides an improved process for the preparation of sunitinib malate of formula-I (a),

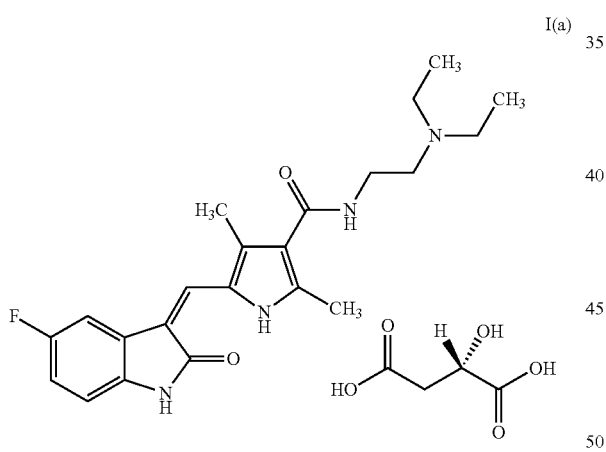

I(a)

which comprises:—
(i) reacting tertiary butylacetoacetate, ethyl acetoacetate, sodium nitrite and Zn dust in acetic acid medium to get a diester derivative of formula-II

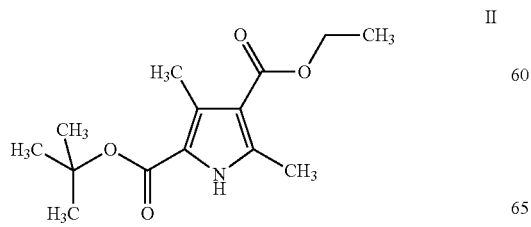

II (ii) selective decarboxylation of compound of formula-II in alcohol-aqueous HCl medium to get half ester derivative of formula-III

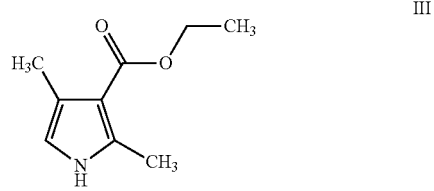

III (iii) formylation at $2^{nd}$ position of pyrrole ring of formula-III using DMF-POCl$_3$ complex to get aldehyde-ester derivative of formula-IV

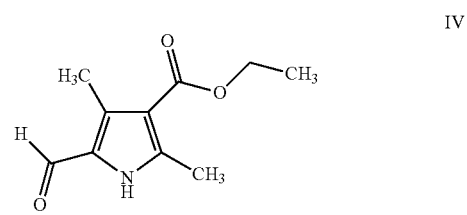

IV (iv) selective hydrolysis of ester moiety of formula-IV using aqueous KOH-alcohol medium to get aldehyde-carboxylic acid derivative of formula-V

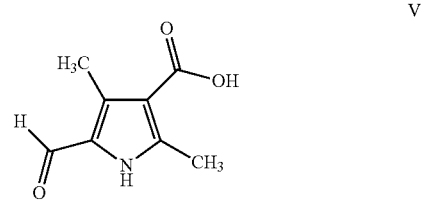

V (v) amidation of carboxylic acid derivative of formula-V using 2-diethyl aminoethyl amine of formula-VI in presence of dicyclohexyl carbodimide and 1-hydroxy benzotriazole to get aldehyde-amide derivative of formula-VII

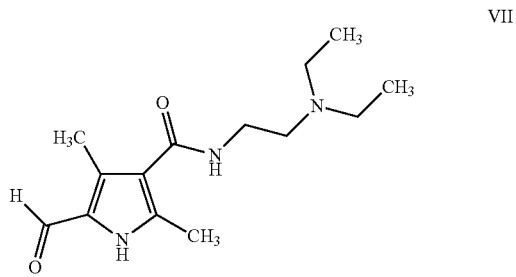 [SMILES: CCN(CC)CCNC(=O)c1c(C)[nH]c(C=O)c1C]

VII (vi) selective reduction carbonyl functionality of 5-fluoro isatin of formula-VIII using aqueous hydrazine hydrate to get 5-fluoro-2-oxindole of formula-IX

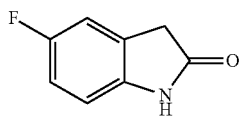

IX (vii) condensation of aldehyde-amide derivative of formula-VII and 5-fluoro-2-oxindole of formula-IX in alcohol medium optionally employing a catalyst to get Sunitinib base of formula-I

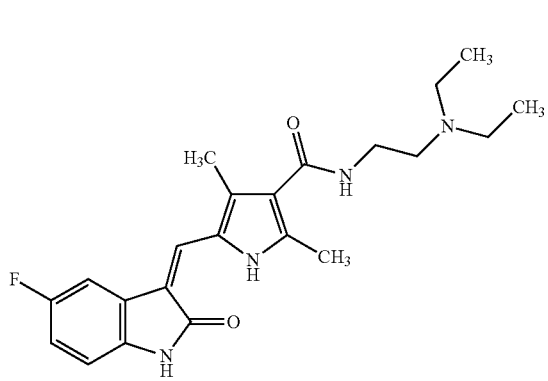

I (viii) conversion of Sunitinib base of formula-I into its pharmaceutically acceptable malate salt of formula-I(a) (1:1 mixture) using L(−)-malic acid in alcohol medium

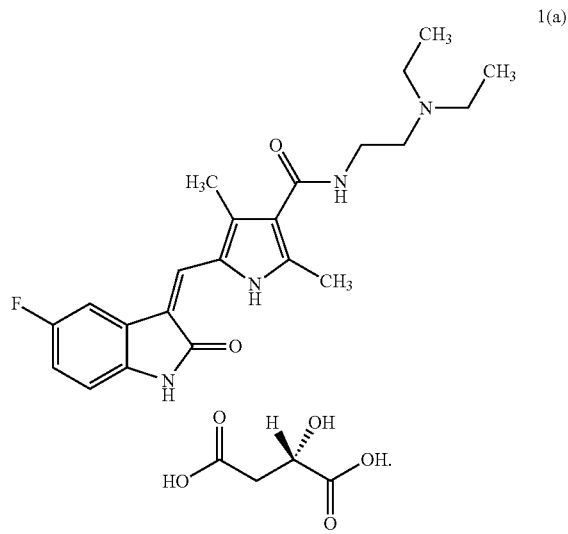

I(a)

(ix) An alternate route of synthesis of compound of formula-I(a), is condensation of intermediate of formula-VII with 5-fluoro-2-oxindole of formula-IX followed by in-situ salt formation of the resulting product with L(−)-malic acid in one step.
(x) Another alternate route of synthesis of compound of formula-I(a), is condensation of intermediate of formula-V with 2-diethylaminoethylamine followed by condensation with 5-fluoro-2-oxindole of formula-IX and L(−)-malic acid in one step.
(xi) purification of Sunitinib malate in a solvent or solvent system to remove impurities or residual solvents from the drug substance.

Additionally, the present invention comprises of the following process details:—

Zinc powder is added in step (i) of Scheme-5 of the present invention, to the reaction mixture containing tertiary butylacetoacetate, ethyl acetoacetate and sodium nitrite in the temperature range of 30-70° C. preferably in the range of 55-70° C.

The reaction mixture is maintained after zinc powder addition in step (i) is in the temperature range of 50-80° C. preferably 65-75° C.

The time of maintenance of the reaction mixture at 65-75° C. in step (i) is 1-4 hours preferably 1-2 hours.

The solvent or solvent mixture employed in step (i) for quenching of the reaction mixture of the product of formula-II is selected from water or water-ethyl acetate or ethyl acetate preferably water.

Quenching of the reaction mixture in step (i) carried out in the temperature range of 50-65° C. preferably at 60-65° C.

The solvent employed in step (i) to extract the product of formula-II is selected from methyl acetate, ethyl acetate or isopropyl acetate preferably ethyl acetate.

The solvent or solvent mixture employed in step (i) to isolate the product of formula-II is selected from water or methanol-water mixture (95:5) or isopropyl alcohol-water (95:5) mixture preferably methanol-water (95:5) mixture.

The volume of the solvent used in step (i) to isolate the product of formula-II is in the range of 1-5 times to its weight, preferably 1-3 times and most preferably 1-2 times of the weight of the product of formula-II and the temperature at which the compound of formula-II can be isolated is in the range of 0-30° C., preferably 0-5° C.

The HPLC purity of compound of formula-II in step (i) after isolation from aqueous methanol is in the range of 99.5-99.8%.

The solvent employed in step (ii) of Scheme-5 of the present invention to knock out one of the ester functions of compound of formula-II is selected from methanol, ethanol or isopropanol preferably isopropanol.

The temperature at which the reaction is maintained in step (ii) is in the range of 40-55° C. preferably 45-50° C.

The HPLC purity of compound of formula-III in step (ii) after isolation is more than 90%.

The solvent employed in the reaction in step (iii) of Scheme-5 of the present invention is selected from dimethyl formamide (DMF), DMF-ethyl acetate or DMF-isopropyl ether preferably DMF.

The solvent or solvent mixture employed in step (iii) for quenching of the reaction mixture of the product of formula-IV is selected from water or water-ethyl acetate preferably water.

The temperature at which quenching of the reaction mixture in step (iii) takes place is in the range of 25-45° C. preferably 25-35° C.

The HPLC purity of compound of formula-IV in step (iii) after isolation is more than 99.5%.

The solvent employed in step (iv) of Scheme-5 of the present invention to extract the compound of formula-V from the reaction mass is selected from ethyl acetate or methyl acetate preferably ethyl acetate.

The temperature at which pH is adjusted in step (iv) is in the range of 0-35° C. preferably 25-30° C.

The temperature at which compound of formula (Iv) is isolated is in the range of 10-40° C. preferably 25-30° C.

The HPLC purity of compound of formula-V in step (iv) after isolation is more than 99.9%.

The coupling reagent employed in step (v) of Scheme-5 of the present invention is dicyclohexyl carbodimide The solvent employed in step (v) is selected from tetrahydrofuran, ethyl acetate preferably tetrahydrofuran.

The solvent employed in step (v) to extract and isolate the product of formula-VII is ethyl acetate.

The temperature at which isolation of compound of formula-VII in step (v) takes place is in the range of 0-30° C. preferably 0-10° C.

The HPLC purity of the compound of formula-VII in step (v) after isolation is more than 99.5%.

The percentage of hydrazine hydrate used to reduce one of the carbonyl functionality of 5-fluoro isatin of formula-VIII in step (vi) of Scheme-5 of the present invention is in the range of 80-99% preferably 90%.

The volume of hydrazine hydrate used in step (vi) is in the range of 1-10 volumes of 5-fluoro isatin of formula-VIII preferably 5 times.

The temperature at which the bath temperature in step (vi) is in the range of 100-150° C. preferably 120-140° C. and most preferably 130-140° C.

The temperature at which isolation of compound of formula-IX in step (vi) takes place is in the range of 0-30° C. preferably 20-30° C.

The HPLC purity of the compound of formula-IX in step (vi) of the present invention after isolation is more than 99.5%.

The solvent employed in the reaction in step (vii) of Scheme-5 of the present invention, is selected from methanol, ethanol, isopropyl alcohol, ethyl acetate, cyclohexane, chloroform, n-hexane, isopropyl ether, toluene, methyl tertiary butyl ether, isopropyl acetate, tetrahydrofuran, preferably methanol, methyl tertiary butyl ether, isopropyl acetate, tetrahydrofuran, isopropyl alcohol and most preferably methanol.

The catalyst used in step (vii) is selected from inorganic bases like ammonia, alkali metal or alkaline earth hydroxides, carbonates, phosphates, bicarbonates and alkali metal hydroxides viz sodium hydroxide, potassium hydroxide or alkaline earth metal hydroxides viz calcium hydroxide, magnesium hydroxide or barium hydroxide, methanolic or ethanolic ammonia, quaternary ammonium compounds like tetra butyl ammonium hydroxide, benzyltrimethyl ammonium hydroxide, silica gel, sodium acetate, ammonium acetate or Lewis acids like Boron trifluoride etherate and organic bases like piperidine, piperazine, pyrrolidine, sodium ethoxide, sodium methoxide, para toluene sulfonic acid (PTSA) preferably pyrrolidine or piperidine and most preferably pyrrolidine.

The temperature at which isolation of Sunitinib of formula-I in step (vii) takes place is in the range of 20-40° C. preferably 25-30° C.

The HPLC purity of the compound of formula-I in step (vii) after isolation is more than 99.7%.

The solvent employed in the reaction in step (viii) of Scheme-5 of the present invention, is selected from methanol, ethanol, isopropyl alcohol, n-butanol, acetone, ethyl acetate, cyclohexane, chloroform, methylene chloride, n-hexane, isopropyl ether, toluene, isopropyl acetate, tetrahydrofuran, 1,4-dioxane, dimethyl formamide, acetonitrile, preferably methanol, methyl tertiary butyl ether, isopropyl acetate, tetrahydrofuran, isopropyl alcohol and most preferably methanol or a mixture thereof.

The solvent used for trituration of the title compound of formula-I(a) to remove residual methanol from the product is selected from ethyl acetate or acetone preferably acetone.

The temperature at which isolation of compound of formula-I(a) in step (viii) takes place is in the range of 20-60° C. preferably 30-50° C.

The temperature at which drying of the compound of formula-I(a) in step (viii) is in the range of 50-100° C. preferably 80-85° C.

The HPLC purity of the compound of formula-I(a) in step (viii) after isolation is more than 99.7%.

The percentage of related impurities in the pharmaceutically acceptable product of formula-I(a) is below 0.10%

Alternatively the product of formula-I(a) can also be prepared in one-pot in step (ix) of Scheme-5 of the present invention by reacting intermediate of formula-VII, 5-fluoro-2-oxindole of formula-IX, L(-)-malic acid, pyrrolidine in alcohol solvent.

The solvent employed in step (ix) is selected from methanol, ethanol, isopropyl alcohol, preferably methanol or ethanol and most preferably methanol.

The temperature at which isolation of Sunitinib malate of formula-I(a) in step (ix) takes place is in the range of 20-40° C. preferably 25-30° C.

The HPLC purity of the compound of formula-I(a) in step (ix) after isolation is more than 99.5%.

By another alternative process, the product of formula-I(a) can also be prepared in one-pot in step (x) of Scheme-5 by reacting intermediate of formula-V, 2-diethylaminoethylamine of formula-VI, 5-fluoro-2-oxindole of formula-IX, L(-)-malic acid, pyrrolidine in alcohol solvent.

The solvent employed in step (x) of Scheme-5 is selected from methanol, ethanol, isopropyl alcohol, tetrahydrofuran preferably methanol, tetrahydrofuran and most preferably methanol.

The temperature at which isolation of Sunitinib malate of formula-I(a) in step (x) takes place is in the range of 20-40° C. preferably 25-30° C.

The HPLC purity of the compound of formula-I(a) in step (x) after isolation is more than 99.2%.

ADVANTAGES OF THE INVENTION

1. The present invention provides an improved process for the preparation and isolation of highly pure Sunitinib malate of formula-I(a).
2. Present process employs easily recoverable, recyclable and environmental friendly reagent like dicyclohexyl carbodimide in amidation step.
3. Present invention produces >99.7% (by HPLC) purity Sunitinib malate with all the impurities below the acceptable limits (0.10%).
4. Present invention avoids highly expensive reagents like 1-(3-dimethylamino-aminopropyl)-3-ethyl carbodimide hydrochloride (EDC), carbonyl diimidazole (CDI), diketene, chloromethylenedimethylammonium chloride, some of which are toxic and difficult to handle.
5. Present invention avoids highly toxic and flammable solvents like methylene, chloride, n-hexane, diethyl ether.
6. Present invention uses environmental friendly, easily recoverable and reusable solvent like ethyl acetate.
7. Present invention provides easily workable procedures and minimizes pollution.
8. Present invention provides easily transferable technology for plant scale production.

Having thus described the present invention with reference to certain preferred embodiments, the invention is further illustrated by the examples, which follow. These examples are provided for illustrative purpose only and are not intended to limit the scope of the invention in any way.

Example 1

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Step (i): Preparation of 3,5-dimethyl-1H-pyrrole-2,4-dicarboxylic acid 2-tertiary butyl ester 4-ethyl ester (II)

Into a 10-L four necked round-bottomed flask equipped with a mechanical stirrer, a thermometer pocket and an air condenser, were charged tertiary butyl acetoacetate (1.0 Kg; 6.3 mole) and acetic acid (3.0 Lt). The solution was cooled to 0-5° C. and a previously dissolved solution of sodium nitrite (0.436 Kg; 6.3 mole) in 640 mL DM water into an addition funnel and added to the flask at a rate that the temperature does not exceed 5° C. After the addition, the solution was maintained for 90 minutes at 0-5° C. and slowly brought the reaction mixture to room temperature (25-30° C.) over a period of 4 hours. At this temperature, ethyl acetoacetate (0.824 Kg; 6.3 mole) was charged at once followed by Zinc powder (0.94 Kg; 14.4 mole) in ten equal lots below 70° C. After addition of zinc powder, the reaction mixture was maintained for 1-2 hours at 65-70° C. The resulting solution was cooled to 60° C. and quenched in a carboy containing 25.0 Lt DM water under stirring. The product was extracted with ethyl acetate and separated using separating funnel. The organic layer was then clarified by treating the product solution with activated charcoal followed by filtration through hyflow. The solvent was then recovered by distillation under diminished pressure and the traces were removed by the addition of methanol (500 ml) to the distillation flask and continued distillation under diminished pressure. The resulting product was triturated in 95% aqueous methanol (1.5 L) at 0-5° C. for 2 hours to get a crystalline product of formula-II.

| Dry Weight: 1.075 Kg | Yield: 63.6% | HPLC Purity: >99.5% |

Step (ii): Preparation of 2,4-dimethyl-1H-pyrrole-3-carboxylic acid ethyl ester (III)

Into a 10-L four necked round-bottomed flask equipped with a mechanical stirrer, a thermometer pocket, gas bubbler and an air condenser, were charged 3,5-dimethyl-1H-pyrrole-2,4-dicarboxylic acid 2-tertiary butyl ester 4-ethyl ester (II) (1.5 Kg; 5.6 mole), isopropyl alcohol 4.5 L and stirred while Conc. HCl (2.2 L) was charged with the aid of addition funnel at 25-30° C. After addition, the temperature of the reaction mixture was raised to 45-50° C. and maintained at this temperature until the gas evolution completely ceases. The reaction was monitored by TLC and the solution cooled to 25-30° C. and quenched in a carboy containing ice water under stirring. The product was isolated by filtration and dried at 50° C.

| Dry Weight: 721.3 g | Yield: 77.3% | HPLC purity: >96% |

Step (iii): Preparation of 5-formyl-2,4-dimethyl-1H-pyrrole-3-carboxylic acid ethyl ester (IV)

Into a 5-L four necked round-bottomed flask equipped with a mechanical stirrer, a thermometer pocket, addition funnel, air condenser and a nitrogen bubbler was charged dimethyl formamide (1.05 L). The solvent was cooled to 0° C. To this chilled solvent, phosphorous oxychloride (0.434 L) was charged at below 5° C. After addition, the temperature of the reaction mixture was slowly brought to 25-30° C. Then a solution of 2,4-dimethyl-1H-pyrrole-3-carboxylic acid ethyl ester (III) (0.7 Kg; 4.2 mole) dissolved in dimethyl formamide (1.05 L) was added drop-wise into the flask at 25-30° C. After addition, the temperature of the reaction mixture was brought to 50° C. and maintained for 2-3 hours. The reaction was monitored by TLC. After maintenance, the reaction mixture was cooled to 25-30° C. and quenched in a carboy containing ice-water. The pH of the solution was then adjusted to 12-13 using aq. KOH solution. After pH adjustment, the solution was stirred at 25-30° C. and filtered and washed with water. The product was dried in a hot air oven at 60° C.

| Dry Weight: 0.753 Kg | Yield: 92% | HPLC purity: >99.9% |

Step (iv): Preparation of 5-formyl-2,4-dimethyl-1H-pyrrole-3-carboxylic acid (V)

Into a 10-L four necked round-bottomed flask equipped with a mechanical stirrer, a thermometer pocket, addition funnel and reflux condenser were charged 5-formyl-2,4-dimethyl-1H-pyrrole-3-carboxylic acid ethyl ester (IV) (0.6 Kg; 3.09 mole), methanol (2.0 L) and aqueous KOH solution (prepared by dissolving 450 g KOH in 1.8 L of water), stirred well and raised the reaction mass temperature to 60-70° C. and maintained for 4-6 hours. The progress of the reaction was monitored by TLC. After completion of the reaction, the excess solvent was removed under diminished pressure and the resulting product was diluted with water and extracted with ethylacetate. The aqueous layer was separated and the pH adjusted to 4.0 with conc. HCl. The resulting solution was stirred over night at 25-30° C. The product was filtered and washed with water. The product was dried at 60° C.

| Dry Weight: 0.483 Kg | Yield: 93.5% | HPLC purity: 99.8% |

Step (v): Preparation of 5-formyl-2,4-dimethyl-1H-pyrrole-3-carboxylic acid (2-diethylaminoethyl)-amide (VII)

Into a 10-L four necked round-bottomed flask equipped with a mechanical stirrer, a thermometer pocket, addition funnel and an air condenser were charged 5-formyl-2,4-dimethyl-1H-pyrrole-3-carboxylic acid (0.25 Kg; 1.5 mole), tetrahydrofuran (3.5 L), dicyclohexyl carbodimide (0.432 Kg), 1-hydroxy benzotriazole (0.306 Kg) and stirred well for 30 minutes. To this solution, a premixed solution of TEA (0.42

L) in tetrahydrofuran (1.25 L) and 2-diethylaminoethyl amine (0.286 L; 2.04 mole) in tetrahydrofuran (1.25 L) were added successively at 25-30° C. After addition, the reaction mixture was stirred for 16 hours at 25-30° C. and the byproduct generated was removed by filtration through filtration funnel. The solvent was removed by distillation under diminished pressure. The resulting product was suspended in DM water and the pH of the slurry adjusted to 12-13 with aqueous NaOH solution. After pH adjustment, the product was extracted with ethyl acetate and washed successively organic layer with aqueous $NaHCO_3$, saturated solution of NaCl and DM water. Organic layer was separated and ¾$^{th}$ of the solvent distilled under diminished pressure. The product was cooled to 0-5° C. and stirred for 2 hours, filtered and washed with chilled ethyl acetate (70 mL). The product was dried at 60° C.

| Dry Weight: 210.2 g | Yield: 53.0% | HPLC purity: 99.95% |
|---|---|---|

Step (vi): Preparation of 5-Fluoro-2-oxindole (IX)

Into a 10-L four necked round-bottomed flask equipped with a mechanical stirrer, a thermometer pocket, and a reflux condenser were charged 5-fluoro-isatin (0.3 Kg; 1.81 mole) and 90% hydrazine hydrate. (1.5 Lt) and stirred well for 30 minutes. The temperature of the reaction mixture was raised to 100-110° C. and maintained for 1 hour and the temperature further raised to 125-130° C. and maintained for 4 hours. The progress of the reaction was monitored by TLC. After completion of reaction, the reaction mixture was cooled to 25-30° C. and diluted with water. The pH was adjusted with conc. HCl to 3.0. The solution was stirred at 25-30° C. for 4 hours. The product was isolated by filtration and washed with ice water. The product was dried at 60° C.

| Dry Weight: 215 g | Yield: 78.4% | HPLC purity: >99.5% |
|---|---|---|

Step (vii): Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 10-L four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (0.35 Kg; 1.32 mole) and 5-Fluoro-2-oxindole (IX) (0.191 Kg; 1.26 mole) and methanol (7.0 L). To this stirred solution pyrrolidine (5.6 mL) was added and heated to reflux for 5-7 hours. The progress of the reaction was monitored by TLC. After completion of reaction, the product solution was filtered and washed with methanol. The wet cake was again triturated in methanol at 60-65° C. for 1 hour, cooled and filtered. The product was dried at 80° C.

| Dry Weight: 410 g | Yield: 78.1% | HPLC purity: >99.7% |
|---|---|---|

Step (viii): Preparation of (2S)-2-hydroxy butane-dioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 10-L four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (550 g; 1.38 mole), L(-)-malic acid (194.4 g; 1.45 mole) and methanol (7.5 L). The solution was then heated to reflux and maintained for 2-4 hours. The bright yellow precipitate was then cooled to 25-30° C. and maintained for 1 hour. Filtered the product and washed the cake with methanol. The wet cake was again taken in to the flask and triturated in methanol at 60-65° C. for 1 hour, cooled to 25-30° C. and maintained for 1 hour and filtered. The wet cake was once again taken in to the flask and triturated finally in acetone at 50-55° C. for 1 hour, cooled to 40-45° C. and maintained for 1 hour and filtered and washed with hot acetone. The product was dried at 80-85° C.

| Dry Weight: 675 g | Yield: 91.8% | HPLC Purity: 99.75% |
|---|---|---|

Example 2

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and methanol (50 mL). To this stirred solution, piperidine (2 drops) was added and heated to reflux for 5-7 hours. The progress of the reaction was monitored by TLC. After completion of reaction, the product solution was filtered and washed with methanol. The wet product was again triturated in methanol at 60-65° C. for 1 hour, cooled and filtered. The product was dried at 80° C.

| Dry Weight: 5.2 g | Yield: 69.3% | HPLC purity: >99.0% |
|---|---|---|

Example 3

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and methanol (50 mL). The solution heated to reflux for 5-7 hours. The progress of the reaction was monitored by TLC. After completion of reaction, the product solution was filtered° and washed with methanol. The wet cake was again triturated in methanol at 60-65° C. for 1 hour, cooled and filtered. The product was dried at 80° C.

| Dry Weight: 3.0 g | Yield: 40% | HPLC purity: >99.1% |

Example 4

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and methanol (50 mL). To this stirred solution sodium bicarbonate (0.5 g) was charged and heated to reflux for 8-10 hours. The progress of the reaction was monitored by TLC. After completion of reaction, the product solution was filtered and washed with methanol. The wet product was again triturated in methanol at 60-65° C. for 1 hour, cooled and filtered. The product was dried at 80° C.

| Dry Weight: 4.0 g | Yield: 53.3% | HPLC purity: >99.5% |

Example 5

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and methanol (50 mL). To this stirred solution potassium hydroxide (0.5 g) was charged and stirred at 25-30° C. for 30 min. The progress of the reaction was monitored by TLC. After completion of reaction, the product solution was filtered and washed with methanol. The wet product was again triturated in methanol at 25-30° C. for 1 hour, cooled and filtered. The product was dried at 80° C.

| Dry Weight: 5.0 g | Yield: 66.6% | HPLC purity: >99.6% |

Example 6

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and methanol (50 mL). To this stirred solution ammonia solution (2-3 drops) was added and stirred at 25-30° C. for 2-4 hours. The progress of the reaction was monitored by TLC. After completion of reaction, the product solution was filtered and washed with methanol. The wet product was again triturated in methanol at 25-30° C. for 1 hour, cooled and filtered. The product was dried at 80° C.

| Dry Weight: 4.2 g | Yield: 56% | HPLC purity: >99.2% |

Example 7

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and methanol (50 mL). To this stirred solution sodium methoxide (0.5 g) was charged and heated to reflux for 10-20 min. The progress of the reaction was monitored by TLC. After completion of reaction, the product solution was filtered and washed with methanol. The wet product was again triturated in methanol at 60-65° C. for 1 hour, cooled and filtered. The product was dried at 80° C.

| Dry Weight: 5.2 g | Yield: 69.3% | HPLC purity: >99.7% |

Example 8

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and methanol (50 mL) To this stirred solution tetra butyl ammonium hydroxide (2-3 drops) was added and heated to reflux for 1-2 hours. The progress of the reaction was monitored by TLC. After completion of reaction, the product solution was filtered and washed with methanol. The wet product was again triturated in methanol at 60-65° C. for 1 hour, cooled and filtered. The product was dried at 80° C.

| Dry Weight: 5.4 g | Yield: 72% | HPLC purity: >99.5% |

Example 9

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked, round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and methanol (50 mL). To this stirred solution potassium fluoride (0.5 g) was charged and heated to reflux for 1-2 hours. The progress of the reaction was monitored by TLC. After completion of reaction, the product solution was filtered and washed with methanol. The wet product was again triturated in methanol at 60-65° C. for 1 hour, cooled and filtered. The product was dried at 80° C.

| Dry Weight: 4.2 g | Yield: 56% | HPLC purity: >99.5% |

Example 10

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and isopropyl alcohol (50 mL). To this stirred solution pyrrolidine (1-2 drops) was added and heated to reflux for 2-4 hours. The progress of the reaction was monitored by TLC. After completion of reaction, the product solution was filtered and washed with isopropyl alcohol. The wet product was again triturated in isopropyl alcohol at 60-65° C. for 1 hour, cooled and filtered. The product was dried at 80° C.

| Dry Weight: 3.6 g | Yield: 48% | HPLC purity: >99.3% |

Example 11

Preparation of N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide—Sunitinib-I Into a 100 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (5.0 g; 0.018 mole) and 5-Fluoro-2-oxindole (IX) (2.73 g; 0.018 mole) and tetrahydrofuran (50 mL). To this stirred solution pyrrolidine (1-2 drops) was added and heated to reflux for 4-6 hours. The progress of the reaction was monitored by TLC. After completion of reaction, the product solution was filtered and washed with tetrahydrofuran. The wet product was again triturated in tetrahydrofuran at 60-65° C. for 1 hour, cooled and filtered. The product was dried at 80° C.

| Dry Weight: 2.0 g | Yield: 26.6% | HPLC purity: >99.5% |

Example 12

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and acetone (35 mL). The solution was then heated to reflux and maintained for 2-4 hours. The bright yellow precipitate was then cooled to 40-45° C. and maintained for 1 hour, the product filtered and washed with acetone. The product was dried at 80-85° C.

| Dry Weight: 2.5 g | Yield: 93.6% | HPLC Purity: >99.5% |

Example 13

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and isopropyl alcohol (35 mL). The solution was then heated to reflux and maintained for 2-4 hours. The bright yellow precipitate was then cooled to 30-35° C. and maintained for 1 hour, the product filtered and washed with isopropyl alcohol. The product was dried at 80-85° C.

| Dry Weight: 2.4 g | Yield: 89.8% | HPLC Purity: >99.65% |

Example 14

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and ethanol (35 mL). The solution was then heated to reflux and maintained for 2-4 hours. The bright yellow precipitate was then cooled to 30-35° C. and maintained for 1 hour, the product filtered and washed with ethanol. The product was dried at 80-85° C.

| Dry Weight: 2.5 g | Yield: 93.6% | HPLC Purity: >99.7% |
|---|---|---|

Example 15

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and acetonitrile (35 mL). The solution was then heated to reflux and maintained for 2-4 hours. The bright yellow precipitate was then cooled to 30-35° C. and maintained for 1 hour, the product filtered and washed with acetonitrile. The product was dried at 80-85° C.

| Dry Weight: 2.4 g | Yield: 89.8% | HPLC Purity: >99.5% |
|---|---|---|

Example 16

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and chloroform (35 mL). The solution was then heated to reflux and maintained for 2-4 hours. The bright yellow precipitate was then cooled to 30-35° C. and maintained for 1 hour, the product filtered and washed with chloroform. The product was dried at 80-85° C.

| Dry Weight: 1.0 g | Yield: 37.4% | HPLC Purity: >99.45% |
|---|---|---|

Example 17

Preparation of (2S)-1-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole); L(−)-malic acid (0.67 g; 0.005 mole) and toluene (35 mL). The solution was then heated to reflux and maintained for 2-4 hours. The bright yellow precipitate was then cooled to 30-35° C. and maintained for 1 hour, the product filtered and washed with toluene. The product was dried at 80-85° C.

| Dry Weight: 1.4 g | Yield: 52.4% | HPLC Purity: >99.45% |
|---|---|---|

Example 18

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser was charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and tetrahydrofuran (35 mL). The solution was then heated to reflux and maintained for 2-4 hours. The bright yellow precipitate was then cooled to 30-35° C. and maintained for 1 hour, the product filtered and washed with tetrahydrofuran. The product was dried at 80-85° C.

| Dry Weight: 1.6 g | Yield: 59.9% | HPLC Purity: >99.5% |
|---|---|---|

Example 19

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and cyclohexane-water mixture. The solution was then heated to reflux and maintained for 2-4 hours. The bright yellow precipitate was then cooled to 30-35° C. and maintained for 1 hour, the product filtered and washed with cyclohexane. The product was dried at 80-85° C.

| Dry Weight: 2.3 g | Yield: 86.1% | HPLC Purity: >99.5% |

Example 20

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and 15% aqueous n-butanol (115 mL). The solution was then heated to reflux and maintained for 2-4 hours. The bright yellow precipitate was then cooled to 30-35° C. and maintained for 1 hour, the product filtered and washed with n-butanol. The product was dried at 80-85° C.

| Dry Weight: 2.5 g | Yield: 93.6% | HPLC Purity: >99.5% |

Example 21

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and 19% aqueous methanol (119 mL). The solution was then heated to reflux and maintained for 2-4 hours. The bright yellow precipitate was then cooled to 30-35° C. and maintained for 1 hour, the product filtered and washed with methanol. The product was dried at 80-85° C.

| Dry Weight: 2.3 g | Yield: 86.1% | HPLC Purity: >99.5% |

Example 22

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 250 mL four necked round-bottomed flask equipped with a mechanical stirrer, a thermometer pocket, and a reflux condenser were charged N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (Sunitinib) (I) (2.0 g; 0.005 mole), L(−)-malic acid (0.67 g; 0.005 mole) and 20% aqueous acetonitrile (120 mL). The solution was then heated to reflux and maintained for 2-4 hours. The bright yellow precipitate was then cooled to 30-35° C. and maintained for 1 hour, filtered the product, washed with acetonitrile and dried at 80-85° C.

| Dry Weight: 1.8 g | Yield: 67.4% | HPLC Purity: >99.57% |

Example 23

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 500 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (10.0 g; 0.03 mole), 5-fluoro-2-oxindole (5.46 g; 0.03 mole) and ethanol (70 mL). The reaction mixture was then heated to refluxed for 8-10 hours. The progress of the reaction was monitored by TLC. After completion of reaction, L(−)-malic acid (3.9 g; 0.029 mole) was charged and further maintained at reflux temperature for 4-6 hours. After maintenance, the reaction mixture was cooled to room temperature and filtered the solids. The wet solids were then triturated in acetone (60 mL) at reflux temperature for 1 hour and cooled to room temperature. The product was isolated by filtration and dried at 80-85° C.

| Dry Weight: 14.3 g | Yield: 71.0% | HPLC Purity: >99.5% |

Example 24

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 500 mL four necked round-bottomed flask equipped with a mechanical stirrer, a thermometer pocket, and a reflux condenser were charged 5-formyl-2,4-dimethyl-1H-pyrrole-3-carboxylic acid (2-diethylaminoethyl)-amide (VII) (10.0 g; 0.03 mole), 5-fluoro-2-oxindole (5.46 g; 0.03 mole) and methanol (70 mL). The reaction mixture was then heated to refluxed for 8-10 hours. The progress of the reaction was monitored by TLC. After completion of reaction, L(−)-malic acid (3.9 g; 0.029 mole) was charged and further maintained at reflux temperature for 4-6 hours. After maintenance, the reaction mixture was cooled to room temperature and filtered the solids. The wet solids were then triturated in acetone (60 mL) at reflux temperature for 1 hour and cooled to room temperature. The product was isolated by filtration and dried at 80-85° C.

| Dry Weight: 14.0 g | Yield: 70% | HPLC Purity: >99.5% |

Example 25

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 500 mL four necked round-bottomed flask equipped with a mechanical stirrer, a thermometer pocket, a nitrogen bubbler, and a reflux condenser were charged 5-formyl-2,4-dimethyl-1H-pyrrole-3-carboxylic acid (V) (10.0 g; 0.06 mole), 1-Hydroxy benzotriazole (12.0 g), dicyclohexylcarbodiimide (17.2 g) and tetrahydrofuran (150 mL). To this stirred solution, a solution of triethyl amine (16.8 mL) in 65 mL tetrahydrofuran followed by N,N-diethylaminoethyl amine (10 mL; 0.07 mole) in 65 mL tetrahydrofuran were added through addition funnel and stirred for 20 hours. The progress of the reaction was monitored by TLC. After completion of reaction, the urea derivative was filtered off and the filtrate was re-charged into a fresh 500 mL round-bottomed flask equipped with a mechanical stirrer, thermometer pocket, a nitrogen bubbler, and a reflux condenser. To this stirred solution L(-)-malic acid (8.9 g; 0.06 mole) was charged and further maintained for 4-6 hours. To the resulting solution, 5-fluoro-2-oxindole (8.99 g; 0.06 mole) was charged and continued at reflux temperature for 4-6 hours. The yellow crystalline precipitate was filtered off and wet cake was washed with tetrahydrofuran (50 mL). The product was again triturated in tetrahydrofuran (70 mL) at reflux temperature for 1 hour and filtered. The product was dried at 80-85° C.

| Dry Weight: 21.5 g | Yield: 67.0% | HPLC Purity: >99.5% |

Example 26

Preparation of (2S)-2-hydroxy butanedioic acid compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)—Sunitinib Malate-I(a)

Into a 500 mL four necked round-bottomed flask equipped with a mechanical stirrer, a thermometer pocket, a nitrogen bubbler, and a reflux condenser were charged 5-formyl-2,4-dimethyl-1H-pyrrole-3-carboxylic acid (V) (10.0 g; 0.06 mole), 1-Hydroxy benzotriazole (12.0 g), dicyclohexylcarbodiimide (17.2 g) and tetrahydrofuran (150 mL). To this stirred solution, a solution of triethyl amine (16.8 mL) in 65 mL tetrahydrofuran followed by N,N-diethylaminoethyl amine (10 mL; 0.07 mole) in 65 mL tetrahydrofuran were charged through addition funnel and stirred for 20 hours. The progress of the reaction was monitored by TLC. After completion of reaction, the urea derivative was filtered off and the filtrate is concentrated. The resulting residue is re-dissolved in methanol (100 mL). To this stirred solution L(-)-malic acid (8.9 g; 0.06 mole) was charged and further maintained for 4-6 hours. To the resulting solution, 5-fluoro-2-oxindole (8.99 g; 0.06 mole) was charged and continued at reflux temperature for 4-6 hours at reflux temperature. The yellow crystalline precipitate was filtered off and wet cake was washed with methanol (50 mL). The product was again triturated in acetone (70 mL) at reflux temperature for 1 hour and filtered. The product was dried at 80-85° C.

| Dry Weight: 19.6 g | Yield: 61.6% | HPLC Purity: >99.5% |

We claim:

1. A process for the peparation of high purity sunitinib malate of formula-I(a),

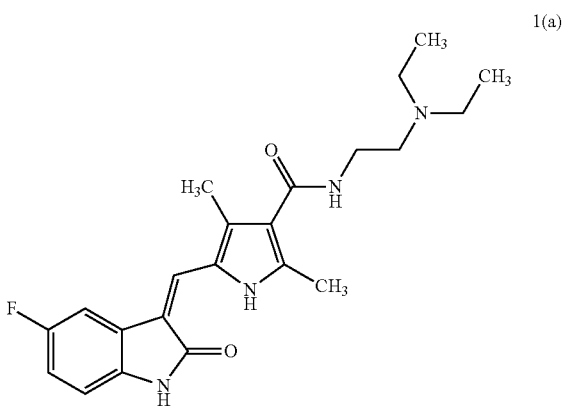

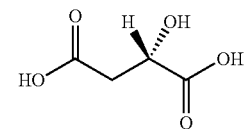

which comprises:—

(i) reacting tertiary butylacetoacetate, ethyl acetoacetate, sodium nitrite and Zn dust in acetic acid medium to get a diester derivative of formula-II

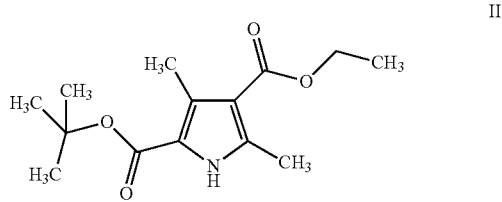 [SMILES: CCOC(=O)c1c(C)[nH]c(C(=O)OC(C)(C)C)c1C]

(ii) selective decarboxylation of compound of formula-II in alcohol-aqueous HCl medium to get half ester derivative of formula-III III
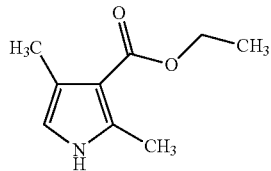

(iii) formylation at 2$^{nd}$ position of pyrrole ring of formula-III using DMF-POCl$_3$ complex to get aldehyde-ester derivative of formula-IV IV
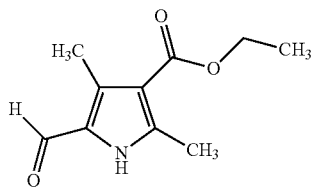

(iv) selective hydrolysis of ester moiety of formula-IV using aqueous KOH-alcohol medium, extracting unreacted compound of formula-IV using an organic solvent and isolating the aqueous solution by adjusting the pH to get aldehyde-carboxylic acid derivative of formula-V V
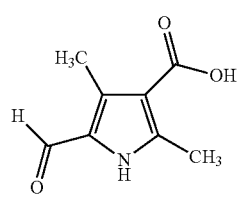

(v) amidation of carboxylic acid derivative of formula-V using 2-diethyl aminoethyl amine of formula-VI in presence of dicyclohexyl carbodimide and 1-hydroxy benzotriazole to get aldehyde-amide derivative of formula-VII VII
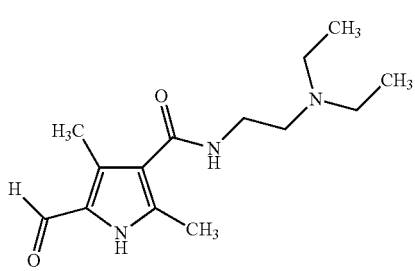

(vi) selective reduction of carbonyl functionality of 5-fluoro isatin of formula-VIII using aqueous hydrazine hydrate to get 5-fluoro-2-oxindole of formula-IX IX
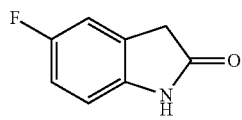

(vii) condensation of aldehyde-amide derivative of formula-VII and 5-fluoro-2-oxindole of formula-IX in alcohol medium optionally employing a catalyst to get Sunitinib base of formula-I I
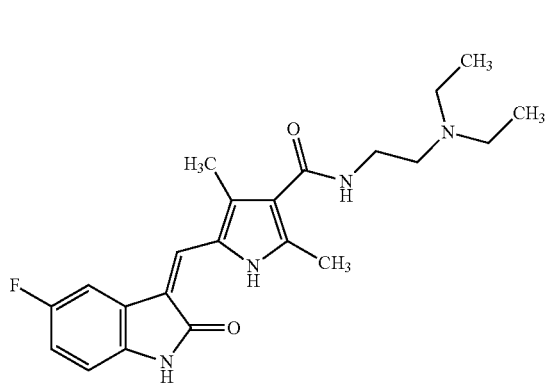

(viii) conversion of Sunitinib base of formula-I into its pharmaceutically acceptable malate salt of formula-I(a) (1:1 mixture) using L(−)-malic acid in an organic solvent I(a)
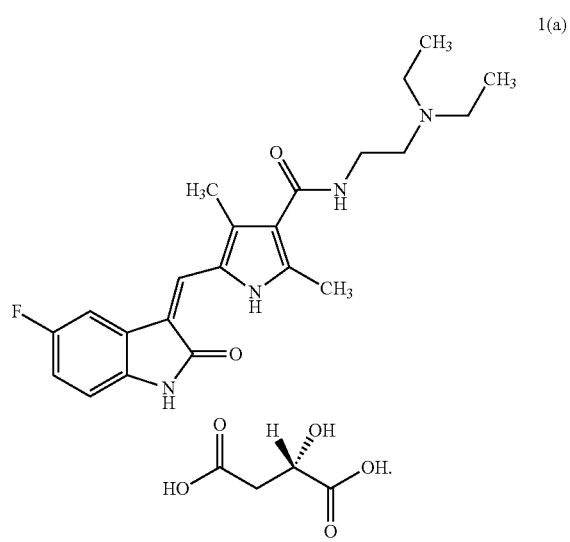

2. A process according to claim 1, wherein, in step (i),
(a) the temperature at which zinc powder added to the reaction mixture is in the range of 30-70° C.; and/or
(b) the temperature at which the reaction mixture is maintained after zinc powder addition is in the range of 50-80° C.; and/or (c) a solvent or solvent mixture selected from water, water-ethyl acetate, and ethyl acetate, is employed for quenching the reaction mixture of the product of formula-II; and/or (d) a solvent selected from methyl acetate, ethyl acetate and isopropyl acetate, is employed to extract the product of formula-II; and/or (e) a solvent or solvent mixture selected from water, methanol-water mixture (95:5), and isopropyl alcohol-water (95:5) mixture, is employed to isolate the product of formula-II.

3. A process according to claim 1 wherein in step (ii) a solvent chosen from methanol, ethanol or isopropanol, is employed to decarboxylate selectively the compound formula-II.

4. A process according to claim 1, wherein in step (iii) a solvent selected from dimethyl formamide (DMF), DMF-ethyl acetate or DMF-isopropyl ether, is employed in the reaction.

5. A process according to claim 1 wherein in step (iv)
(a) a solvent selected from ethyl acetate and methyl acetate, is employed to extract the unreacted compound of formula IV from the reaction mass.

6. A process according to claim 1, wherein the temperature at which compound of formula V is isolated is in the range of 10-40° C.

7. A process according to claim 1 wherein in step (v) a dicyclohexyl carbodiimide coupling reagent is employed, and a solvent is employed.

8. A process according to claim 7, wherein ethyl acetate is employed in step (v) to extract and isolate the product of formula-VII.

9. A process according to claim 1 wherein the percentage of hydrazine hydrate used to reduce one of the carbonyl functionality of 5-fluoro isatin of formula-VIII in step (vi) is in the range of 80-99%, preferably 90%.

10. A process according to claim 1 wherein in step (vii) a solvent selected from methanol, ethanol, isopropyl alcohol, ethyl acetate, cyclohexane, chloroform, n-hexane, isopropyl ether, toluene, methyl tertiary butyl ether, isopropyl acetate, and tetrahydrofuran is employed in the reaction.

11. A process according to claim 1, wherein in step (viii) a solvent selected from methanol, ethanol, isopropyl alcohol, n-butanol, acetone, ethyl acetate, cyclohexane, chloroform, methylene chloride, n-hexane, isopropyl ether, toluene, isopropyl acetate, tetrahydrofuran, 1,4-dioxane, dimethyl formamide and acetonitrile is employed in the reaction, and in step (viii) a solvent is used for trituration of the title compound of formula-1(a).

12. A process according to claim 1, wherein the product of formula-I(a) is prepared in one-pot by reacting the intermediate of formula-VII, 5-fluoro-2-oxindole of formula-IX, L(−)-malic acid, pyrrolidine in alcohol solvent.

13. A process according to claim 12, wherein the solvent is selected from methanol, ethanol and isopropyl alcohol.

14. A process according to claim 1 wherein the product of formula-I(a) is prepared in one-pot by reacting the intermediate of formula-V, 2-diethylaminoethylamine of formula-VI, 5-fluoro-2-oxindole of formula-IX, L(−)-malic acid, pyrrolidine in alcohol solvent.

15. A process according to claim 14 wherein the solvent employed is selected from methanol, ethanol, isopropyl alcohol, and tetrahydrofuran.

16. A process according to claim 2, wherein, in step (i),
(a) the temperature at which zinc powder added to the reaction mixture containing tertiary butylacetoacetate, ethyl acetoacetate and sodium nitrite is in the range of 55-70° C.; and/or
(b) the temperature at which the reaction mixture is maintained after zinc powder addition is in the range of 65-75° C.; and/or
(c) the solvent or solvent mixture employed for quenching the reaction mixture of the product of formula-II is water; and/or
(d) the solvent employed to extract the product of formula-II is ethyl acetate; and/or
(e) the solvent or solvent mixture employed to isolate the product of formula-II is a methanol-water (95:5) mixture.

17. A process according to claim 3, wherein in step (ii) the solvent isopropanol is employed to decarboxylate selectively the compound formula-II.

18. A process according to claim 17, wherein the temperature at which the reaction is maintained in step (ii) is in the range of 35-40° C.

19. A process according to claim 4, wherein in step (iii) the solvent DMF is employed in the reaction.

20. A process according to claim 6, wherein in step (iv) the temperature at which pH is adjusted is in the range of 0-35° C.

21. A process according to claim 20, wherein in step (iv), the temperature at which pH is adjusted is in the range of 25-30° C.

22. A process according to claim 6, wherein the temperature at which compound of formula-V is isolated is in the range of 25-30° C.

23. A process according to claim 7, wherein in step (v) a dicyclohexyl carbodiimide coupling reagent is employed, and a solvent selected from tetrahydrofuran and ethyl acetate, is employed.

24. A process according to claim 23, wherein in step (v) tetrahydrofuran is employed as solvent.

25. A process according to claim 9, wherein the percentage of hydrazine hydrate used to reduce one of the carbonyl functionality of 5-fluoro isatin of formula-VIII in step (vi) is 90%, and step (vi) is performed in a bath at a temperature in the range of 100-150° C.

26. A process according to claim 25, wherein step (vi) is performed in a bath at a temperature in the range of 120-140° C.

27. A process according to claim 10, wherein in step (vii) a solvent selected from methanol, methyl tertiary butyl ether, isopropyl acetate, tetrahydrofuran, isopropyl alcohol is employed in the reaction, and the catalyst used in step (vii) is selected from inorganic bases, alkali metal or alkaline earth hydroxides, carbonates, phosphates, bicarbonates and alkali metal hydroxides, methanolic or ethanolic ammonia, quaternary ammonium compounds, silica gel, sodium acetate, ammonium acetate, Lewis acids and organic bases.

28. A process according to claim 27, wherein in step (vii) the solvent employed in the reaction is methanol, and the catalyst used in step (vii) is selected from ammonia, sodium hydroxide, potassium hydroxide, calcium hydroxide, magnesium hydroxide barium hydroxide, tetrabutyl ammonium hydroxide, benzyltrimethyl ammonium hydroxide, boron trifluoride etheratate, piperidine, piperazine, pyrrolidine, sodium ethoxide, sodium methoxide, or para-toluenesulfonic acid (PTSA).

29. A process according to claim 28, wherein the catalyst used in step (vii) is selected from pyrrolidine or piperidine.

30. A process according to claim 29, wherein the catalyst used in step (vii) is pyrrolidine.

31. A process according to claim 11, wherein in step (viii) a solvent selected from methanol, acetone, methyl tertiary butyl ether, isopropyl acetate, tetrahydrofuran, isopropyl alcohol, is employed in the reaction, and in step (viii) a solvent selected from ethyl acetate and acetone, is used for trituration of the title compound of formula-I(a) to remove residual methanol from the product.

32. A process according to claim 31, wherein in step (viii) methanol or acetone or a mixture thereof is employed in the reaction, and in step (viii) acetone is used as solvent for trituration of the title compound of formula-I(a) to remove residual methanol from the product.

33. A process according to claim 13, wherein the solvent is selected from methanol or ethanol.

34. A process according to claim 33, wherein the solvent is methanol.

35. A process according to claim 15, wherein the solvent employed is selected from methanol or tetrahydrofuran.

36. A process according to claim 35, wherein the solvent employed is methanol.

* * * * *